United States Patent [19]

Marsoner

[11] 4,443,763
[45] Apr. 17, 1984

[54] METHOD AND AN APPARATUS FOR CHECKING POLAROGRAPHIC MEASURING ELECTRODES

[75] Inventor: Hermann Marsoner, Graz, Austria

[73] Assignee: Hans List, Graz, Austria

[21] Appl. No.: 302,786

[22] Filed: Sep. 16, 1981

[30] Foreign Application Priority Data

Sep. 18, 1980 [AT] Austria ............................ 4678/80

[51] Int. Cl.³ .......................................... G01N 27/02
[52] U.S. Cl. ................................ 324/439; 324/71.1; 204/401
[58] Field of Search ............... 324/439, 71.1, 65 CR, 324/133, 123 C; 204/194, 400, 401, 402, 403

[56] References Cited

U.S. PATENT DOCUMENTS

| 4,037,153 | 7/1977 | Kalanit | 324/133 |
| 4,181,882 | 1/1980 | Isaacs et al. | 324/71.1 |
| 4,223,549 | 9/1980 | Kitzinger | 204/401 |

Primary Examiner—Michael J. Tokar
Assistant Examiner—Kevin D. O'Shea
Attorney, Agent, or Firm—Watson, Cole, Grindle & Watson

[57] ABSTRACT

The measuring electrode to be checked is polarized cyclically with an alternating voltage and the maximum amplitude of the electrode current as occuring during cyclical polarization is directly used as a measure for the metrologically relevant condition of the electrode.

8 Claims, 5 Drawing Figures

METHOD AND AN APPARATUS FOR CHECKING POLAROGRAPHIC MEASURING ELECTRODES

BACKGROUND OF THE INVENTION

The present invention relates to a method for checking the condition of polarographic measuring electrodes, particularly oxygen electrodes, by means of cyclical voltammetry, wherein the measuring electrode is polarized with an alternating, preferably delta voltage and wherein the sensitivity of the resulting electrode current to the behaviour of the polarization voltage serves to yield an indication of the condition of the measuring electrode. The invention further also relates to an arrangement for implementation of the aforesaid method.

DESCRIPTION OF THE PRIOR ART

For measuring the partial gas pressure in fluids or gas mixtures measuring electrodes are used today in a wide range of applications, particularly in medicine, such measuring electrodes being constructed and working by the principles of polarography. Such measuring electrodes are provided with a cathode and an anode jointly arranged within an electrolyte solution. The entire system is closed toward the exterior by means of a thin membrane stretched flat over the cathode and permeable by the gas to be detected.

Determination, for instance, of oxygen with such a polarographic oxygen electrode, will ensue by applying a polarization voltage to the electrode system, wherein the oxygen reaching the cathode by diffusion is reduced at the cathode with concomitant absorption of electrons. The diffusion-limiting current which is developing in case of equilibrium state in the direction towards the cathode and corresponds to a reaction-limiting current represents a measure for the partial oxygen pressure in the medium surrounding the measuring sensor. In measuring practice the following three properties of polarographic measuring electrodes are of decisive importance:

(a) Sensitivity: This is the detectable electrode current per unit of partial pressure of the gas to be detected. It is generally indicated in nA/mmHg.

(b) Zero current: This is the detectable electrode current with the measuring electrode located in an environment free from the gas to be detected, f.i., oxygen.

(c) Range of linearity: This is the range of partial pressure, wherein a linear concatenation obtains between electrode current and partial pressure.

For the application of such measuring electrodes in metrology a possibly long duration is desired for the constancy of sensitivity, as is a low zero current and a wide range of linearity. The usual known constructions of polarographic oxygen electrodes are provided with a platinum or gold cathode and a silver anode.

Freshly prepared measuring electrodes, in which the surfaces of cathodes as well as anodes are very pure and have not yet been subjected to any reactions, will generally very well fulfill the requirements of adequate sensitivity, low zero current and wide range of linearity. These properties will, however, change with an increasing duration of use and this will bring about an undesirable and intolerable interference with measurements.

It is above all two processes ensuing independent of each other which have a governing influence on the aforegoing. On one hand, decomposition will occur of the metallic silver at the anode whereupon silver cations will wander in the electric field to the cathode where they are discharged and will again precipitate as metallic silver at the cathode. Since the cathodic reaction of oxygen can ensue also at the precipitated silver, the reactive surface of the cathode is increased and the detectable electrode current will rise, the partial pressure remaining constant herein. Insofar as this process of silver precipitation at the cathode is ensuing unimpeded to a high degree, the electrode current prevailing during the measurement will increase at such a rate that the measuring electrode is no longer suitable for sensing a relevant measuring value. On the other hand, a further process, the details of which are unknown to a high degree, will ensue at the electrodes and negatively influence the catalytic properties of the cathode material. It is assumed that this involves processes of oxidation of the noble-metal cathode, and that thereby an impediment is created to those steps of the reaction at the cathode which govern the rate of reaction.

This will manifest itself by a severe limitation of the range of linearity, an increase in the residual current, and a strongly reduced electrode sensitivity.

It is known from Austrian Patent Specification 358 532 that the aforenamed processes, which have a direct influence upon metrologically important properties of the measuring electrodes, may be determined and differentiated by the method of cyclic voltammetry. To establish a cyclical polarogramm, the polarographic measuring electrode to be checked is polarized by applying an alternating delta voltage. It proved that with an unused electrode the electrode current of the applied polarization voltage will very closely follow the applied frequency in both directions of polarization. It proved furthermore, that in measuring electrodes with silver precipitation at the cathode surface a characteristic curve line will develop in the cyclical polarogram having a distinct peak upon polarization in the cathodic direction, and also upon repolarization in the anodic direction. The fact that the peak in the cyclical polarogram is the result of silver precipitations at the cathode was proven by numerous confirming tests. In measuring electrodes with strongly advanced oxidative changes at the cathode the cyclical polarogram would show a strongly developed hysteresis, which became even more distinct with an increasing frequency of the polarization voltage. It was concluded from this fact that the change in the condition of the cathode will ensue concomitant with a change in one of those steps of the reaction which govern the reaction rate.

It is thus possible with this known method, to obtain indications on changes in the condition of the checked polarographic measuring electrode and to correlate to the aforedescribed processes particularly the deterioration of those electrode properties which are important for the measurement.

SUMMARY OF THE INVENTION

It is an objective of the present invention to furnish a method by which, proceeding from the initially named known measuring method, an improvement is obtained in checking the condition of polarographic measuring electrodes in such a way, that an indication of the metrologically relevant quality of the measuring electrode may be derived directly from such checking.

According to the present invention this is attained by the maximum amplitude of the electrode current as occuring during cyclical polarization of the measuring electrode being directly used as a measure of the metrologically relevant quality of the measuring electrode. Other forms of the applied alternating polarization voltage may be used herein, but it proved that a delta voltage at a frequency of approx. 0.1 Hz and a unilateral peak amplitude of approx. 900 mV will bring best results. Sine-shaped voltages are also practicable as are exponentially shaped voltages or-with some disadvantages—also alternating rectangular-pulse voltages. It then proved unexpectedly that the height of the maximum prevailing electrode current is a direct quality indicator for the metrologically relevant condition of the measuring electrode, irrespective of the aforenamed interferences occuring each by itself or in combination. It is thus practicable in a particularly simple and advantageous manner to obtain an indication of measuring-electrode quality by measuring the height of the maximum prevailing electrode current.

According to a further proposition of the present invention provision is made for the amplitude range of the electrode current prevailing during cyclical polarization to be divided according to trigger levels into a minimum of two ranges, each correlated to a quality grade, so that exceeding the individual trigger levels will serve for classing a checked measuring electrode into a quality grade correlated to the maximum trigger level which has been exceeded in the respective instance.

Classification of the checked measuring electrode and its correlation to a quality grade is thus being made according to the amplitude which had been just exceeded by the electrode current. Provision may then be made, for instance in the operating instructions for the measuring electrode, that certain quality grades will allow only restricted use or that upon exceeding a certain trigger level the electrode must be taken out of use and subjected to regeneration, for instance mechanical removal of deposits.

Since it was furthermore proved that the current-voltage characteristic of the first polarization period will on occasion considerably differ from that of subsequent periods, it is provided in a modification of the method as per invention, to use the prevailing electrode current for determining the prevailing condition of the measuring electrode only after a minimum of one polarization cycle has been run. It will thus be ensured that a relevant indicating of the condition of the polarographic measuring electrode can be obtained also under unfavorable conditions.

An arrangement for implementing the aforedescribed method, as per the invention, provides a measuring network in which the anode of the measuring electrode is connected to one pole of an alternating voltage source for polarization and the cahode of the measuring electrode to a current amplifier, is constructed, according to a further feature of the present invention, in such a manner that the voltage delivered by the current amplifier, which is proportional to the electrode current, is applied to a trigger circuit with at least one trigger level. The trigger circuit is connected to an indicating unit, which in turn effects an indication corresponding either to the respectively highest exceeded trigger level or to the quality grade correlated to the latter. It is of particular advantage in this connection to interpose a rectifier between the current amplifier and the trigger circuit so that the negative amplitudes of the electrode current are also included into the determination, and these amplitudes will not require their own trigger levels.

As per a particularly preferred embodiment of the present invention provision is made for the trigger circuit to have two trigger levels, the lower of which marking the upper limit of an electrode current identifying a fully perfect functioning measuring electrode, and the higher level marking the lower limit of an electrode current identifying an unusable measuring electrode. Three quality grades will result, thus allowing evaluation of the condition of the measuring electrode to a degree fully adequate in normal measuring operations. As long as the lowest trigger is not being reached by the electrode current the measuring electrode will, for instance, be classified as "perfect"; upon exceeding the first trigger level the trigger circuit will supply a corresponding signal to the indicating unit wherein the indication as effected may, for instance, be correlated to a classification "restricted usability"; upon exceeding the upper trigger level the checked measuring electrode will be classified "unusable". It thus becomes practicable to check polarographic measuring electrodes, particularly oxygen electrodes, in a simple and rapid manner with the particular advantage that no stabilizing phase is required and that such examination may always be performed under normal room atmosphere with no calibrating gases being required.

It is furthermore possible by using the method as per the present invention to check such measuring electrodes without the selectively permeable membrane located over cathode and anode as usually required. For this purpose the measuring-sensitive portion of the membraneless measuring electrode is, for instance, brought into contact with an aqueous neutral soluting of sodium or potassium chloride, the concentration of said soluting being per se of secondary importance but preferably being approximately 0.1 mol/l. The solution should have a partial oxygen pressure identical to that of the surrounding atmosphere. Although in this instance conditions may prevail under which different amplitudes of the electrode current will occur during polarization, the polarogram and, respectively, the relevance of its indication remain identical, so that no changes will occur in the method for checking the condition of polarigraphic measuring electrodes.

In further modification of the present invention the indicating unit may also be connected to luminous indicating displays energized according to the respectively exceeded highest trigger level, thus giving an optical indication of the corresponding quality grade of the measuring electrode. This serves to simplify the checking of the condition and will exclude to a high degree reading errors by operating personnel.

DESCRIPTION OF THE DRAWINGS

The present invention is explained in more detail below with the aid of the accompanying drawings, wherein.

DESCRIPTION OF A PREFERRED EMBODIMENT

The cyclical polarograms shown in FIGS. 1 to 3 and 5 were established with oxygen electrodes that had been polarized with a delta voltage at a frequency of 0.1 Hz and a peak amplitude of the polarizaton voltage of 900 mV. Polarograms of far-reaching similarity are however also obtained on polarization of the electrode with a sine voltage or a cyclical alternating voltage having an exponential pulse rise. In all polarograms shown the negative polarization voltage $-U_p$ is entered on the abscissa in the positive direction, and the respectively identifiable electrode current $I_p$ is entered on the ordinate.

Figure 1:
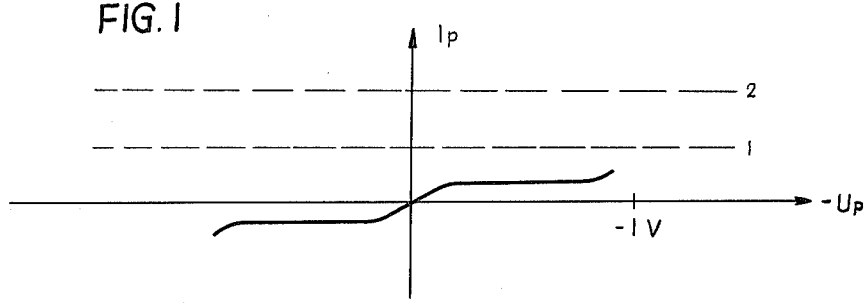
FIGS. 1, 2, 3 and 5 show characteristic curves relating to electrode current/polarization voltage in polarographic oxygen electrodes.

FIG. 1 shows the cyclical polarogram of a catalyically perfect freshly prepared oxygen electrode entered in a thick line. The characteristic feature therein is that a clearly recognizable current plateau has been formed at both sides of the curves, i.e., toward negative and also the positive polarization voltages, thus showing that with rising polarization voltage $U_p$ the electrode current $I_p$ will not significantly increase before a limiting voltage has been reached. Upon the polarization voltage $U_p$ rising further and above such limiting voltage, which would indicate the start of oxygen generation at the measuring electrode, there would be a strong increase in the elctrode current. The maximum amplitude of the polarization voltage is therefore to be so selected that this limiting voltage will just be reached, which can be recognized from the slight bend of the polarogram at the extreme ends. With continually alternating polarization, the electrode current $I_p$ will rather exactly follow the polarization voltage $U_p$ which can be seen by the lack of a distinctly shaped hysteresis of the curve in FIG. 1.

Figure 2:
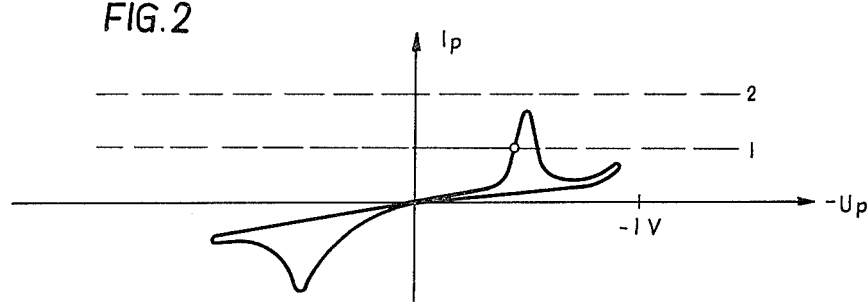

The polarogram in FIG. 2 shows a distinctly shaped peak at a polarization voltage $U_p$ of $-300$ mV and $+100$ mV. Requisite test series allowed proving that the rise of the electrode current $I_p$ at that point is concamitant with an interference reaction in the operation of the oxygen electrode, such interference reaction being interpreted as depositing of silver at the cathode. Such depositing of silver can be ascribed to the metallic silver anodically coming into solution during electrode operation and to the silver ions under the influence of the electric polarization wandering to the cathode being discharged thereat and again deposited on the cathode as metallic silver. It is above all the sensitivity of the measuring electrode which is decisively changed thereby, since the cathodic reaction of the oxygen may also ensue at the deposited silver and the elctrode current, with the partial pressure per se remaining equal, then rising in a stron uncontrollable manner.

Figure 3:
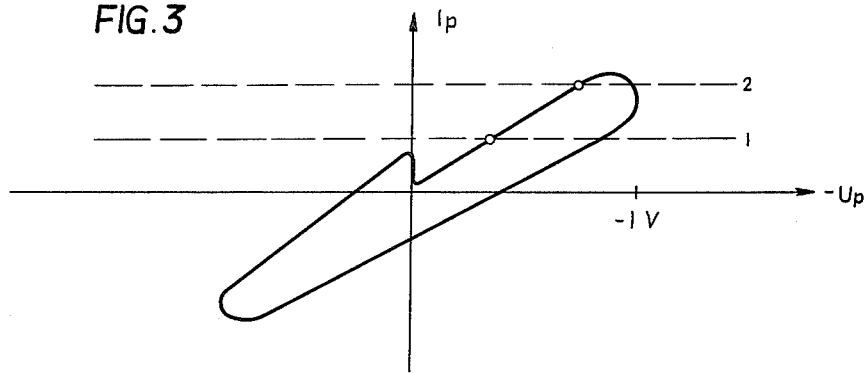

The polarogramm according to FIG. 3 is the result of a further interference reaction, which may probably be ascribed to oxidation of the noble-metal cathode or to an absorption of oxygen at the noble-metal surface or to a chemisorption of oxygen at the cathode surface. Such interference will ensue regularly when polarographic oxygen electrodes are kept in continual operation throughout a longer period. Those reaction steps which determine the rate of reaction at the cathode will be impeded, which will result in a strong restriction of the range of linearity, and increase in the residual current and a strong reduction of electrode sensitivity.

Figure 4:
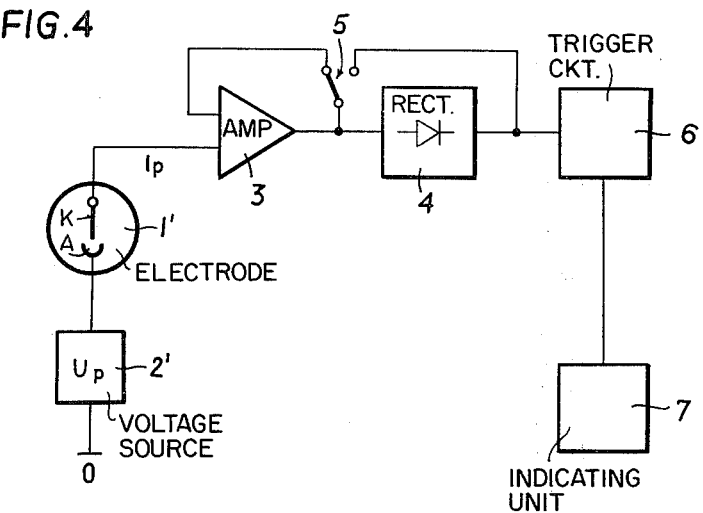
FIG. 4 shows a measuring network of an arrangement for implementing the method as per invention.

The trigger levels 1 and 2 for the electrode current $I_p$, entered as broken lines parallel to the abscissa in FIGS. 1 to 3, will be discussed below in concatenation with the measuring network for the cyclical polarization, particularly of oxygen electrodes, as shown in FIG. 4. According to FIG. 4 a polarographic oxygen electrode 1' is connected with its noble-metal cathode K to a customary current amplifier 3 and with its anode A to one pole of a voltage source 2' serving to generate the already discussed alternating polarization voltage $U_p$. The second pole of the voltage source 2' is connected to the network ground 0. The voltage source 2' will, for instance, deliver an alternating delta voltage with a peak amplitude of 900 mV and a frequency in the range from 0.005 Hz to 1 Hz, wherein a frequency of approximately 0.1 Hz has proven optimal.

The electrode current $I_p$ delivered by the measuring electrode 1' is supplied from the output of the current amplifier 3 as proportional voltage and in amplified form through a changeover switch 5, optionally either to a rectifier 4 or directly to a trigger circuit 6. The trigger circuit 6 is connected to an indicating unit 7.

Figure 5:
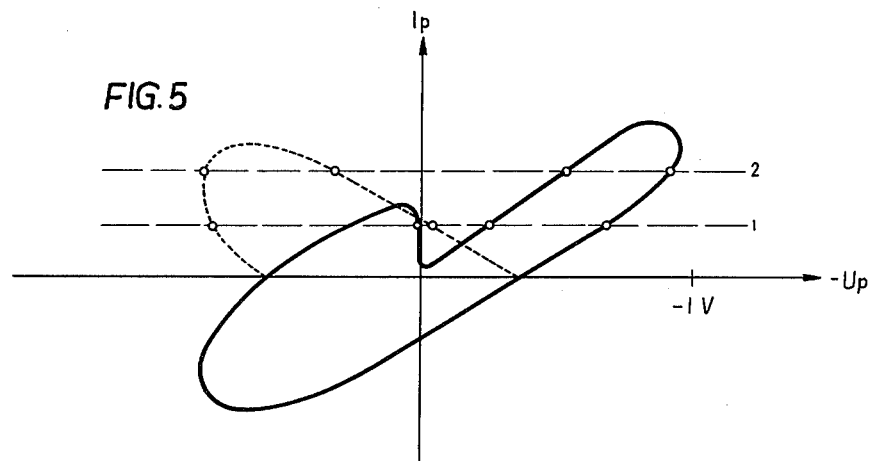

The trigger circuit is, for instance, provided with two trigger levels 1 and 2 as entered in FIGS. 1 to 3 and 5, the lower level 1 marking the upper limit of an electrode current indicating a fully perfect functioning measuring electrode, the higher level 2 marking the lower limit of an electrode current indicating a usable measuring electrode. Insofar as the electrode current $I_p$—as shown in FIG. 1—will not exceed the trigger level 1, an indication conforming to the highest quality grade will be effected by the indicating unit 7. Should the electrode current $I_p$—as shown in FIG. 2—exceed trigger level 1 but not trigger level 2, the indicating unit 7 will, for instance, effect an indication for quality grade "conditionally usable". If—as shown in FIGS. 3 and 5—the electrode current $I_p$ should rise even above the higher trigger level 2, the indicating unit 7 will then display the quality grade "unusable", whereupon the respective electrode must be taken out of the measuring operation and subjected to regeneration.

In FIG. 5 a dotted line indicates the shape of the lower-portion of the polarogram as it will ensue with changeover switch 5 positioned as in FIG. 4; the rectifier 4 is interposed between current amplifier 3 and trigger circuit 6 and will convert negative currents $I_p$ into positive ones. The polarogram entered in FIG. 5 with a solid line would thus result upon requisite changeover of changeover switch 5 in FIG. 4—i.e. upon the rectifier 4 being bridged over.

Any desirable number of trigger levels for the electrode current is conceivable for the electrode current so that the classification of measuring electrodes into quality grades could correspondingly be on a more finely graded scale.

The indicating unit 7 may furthermore also be connected with luminous indicators (not shown herein)., which would be energized according to the respectively exceeded trigger level and which would optically indicate the respective quality grade of the measuring electrode.

The aforegoing will thus result in a very simple and rapid checkability of polarographic measuring electrodes, this being particularly advantageous as no stabilization phase is required, and this test may also be implemented at normal room atmosphere with no calibrating gases of any kind being required. It is also to be noted in this context that the cyclical polarogram of the first voltage cycle may, under certain circumstances, differ very considerably from that of further cycles, and for this reason provision has also been made for the checking of the condition extending over several polarization cycles startable at the voltage source 2'.

I claim:

1. Method for checking the condition of polarographic measuring electrodes by means of cyclical voltammetry, comprising polarizing the measuring electrode with an alternating voltage, detecting the maximum amplitude of the electrode current prevailing during cyclical polarization of the measuring electrode, and determining the quality of the metrologically relevant condition of the measuring electrode from the detected maximum electrode current.

2. Method according to claim 1, wherein a delta voltage is used as the polarization voltage.

3. Method according to claim 1, further comprising dividing the amplitude range of the electrode current prevailing during cyclical polarization by trigger levels into a minimum of two ranges, each correlated to a quality grade, exceeding the individual trigger levels, and classifyiing the checked measuring electrode into a quality grade correlated to the maximum trigger level exceeded in the respective instance.

4. Method according to any of claims 1 to 3, wherein the prevailing electrode current is used for determining the condition of the measuring electrode only after a minimum of one polarization cycle.

5. Apparatus for checking the condition of polarographic measuring electrodes by means of cyclical voltammetry, comprising an alternating voltage source, a current amplifier, and a measuring circuit including a trigger circuit, the anode of the measuring electrode to be checked is connected to one pole of said alternating voltage source for polarization, and the cathode of the measuring electrode is connected to said current amplifier, and wherein the output voltage delivered proportional to the electrode current by said current amplifier is applied to an input of said trigger circuit having at least one trigger level, and an output of said trigger circuit is connected to an indicating unit for effecting an indication corresponding to the highest exceeded trigger level.

6. Apparatus according to claim 5, additionally comprising a rectifier, which is interposed between said current amplifier and said trigger circuit.

7. Apparatus according to any of claims 5 or 6, wherein said trigger circuit has two trigger levels, the lower of which marking the upper limit of an electrode current identifying a fully perfect functioning measuring electrode, and the higher level marking the lower limit of an electrode current identifying an unusable measuring electrode.

8. Apparatus according to claim 7, comprising luminous displays connected to said indicating unit, which are energized corresponding to the respectively highest exceeded trigger level and indicate optically the respective quality grade of the measuring electrode.

* * * * *